(12) United States Patent
Raduma et al.

(10) Patent No.: US 10,401,445 B2
(45) Date of Patent: Sep. 3, 2019

(54) MAGNETIC RESONANCE TRANSMIT AND/OR RECEIVE ANTENNA SYSTEM AND RADIOTHERAPY PLANNING COMPUTER PROGRAM PRODUCT

(71) Applicants: KONINKLIJKE PHILIPS N.V., Eindhoven (NL); IMPAC MEDICAL SYSTEMS, INC., Sunnyvale, CA (US)

(72) Inventors: Wycliffe Adell Raduma, Eindhoven (NL); Annemaria Johanna Halkola, Eindhoven (NL); Michel Moreau, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 160 days.

(21) Appl. No.: 15/506,942

(22) PCT Filed: Sep. 1, 2015

(86) PCT No.: PCT/EP2015/069916
§ 371 (c)(1),
(2) Date: Feb. 27, 2017

(87) PCT Pub. No.: WO2016/034568
PCT Pub. Date: Mar. 10, 2016

(65) Prior Publication Data
US 2017/0276744 A1 Sep. 28, 2017

Related U.S. Application Data

(60) Provisional application No. 62/045,138, filed on Sep. 3, 2014.

(30) Foreign Application Priority Data

Sep. 3, 2014 (EP) .................................... 14183412

(51) Int. Cl.
*G01R 33/34* (2006.01)
*G01R 33/00* (2006.01)
(Continued)

(52) U.S. Cl.
CPC ........ *G01R 33/34038* (2013.01); *A61B 5/055* (2013.01); *A61N 5/1039* (2013.01);
(Continued)

(58) Field of Classification Search
None
See application file for complete search history.

(56) References Cited

U.S. PATENT DOCUMENTS 7,250,764 B2 * 7/2007 Tropp ................... A61B 5/055
324/309
2009/0124887 A1 5/2009 Roell et al.
(Continued)

FOREIGN PATENT DOCUMENTS

EP 1660175 B1 2/2012

*Primary Examiner* — Douglas X Rodriguez
(74) *Attorney, Agent, or Firm* — Sherry Austin

(57) ABSTRACT

A magnetic resonance transmit and/or receive antenna system configured for being used in combination with a magnetic resonance radiotherapy system. The antenna system can include at least one antenna for transmitting and/or receiving radio frequency signals and a cover enclosing the antenna components. The antenna can include antenna components and the cover can include a spatially varying thickness and/or density towards an outer edge of the surface and/or next to an antenna component as to make the change in radiation attenuation between the enclosing cover compared to the antenna component and/or air more gradual.

7 Claims, 8 Drawing Sheets

(51) Int. Cl.
*G01R 33/28* (2006.01)
*H01Q 1/22* (2006.01)
*H01Q 7/00* (2006.01)
*A61N 5/10* (2006.01)
*G01R 33/48* (2006.01)
*A61B 5/055* (2006.01)

(52) U.S. Cl.
CPC ....... *G01R 33/0047* (2013.01); *G01R 33/288* (2013.01); *G01R 33/34007* (2013.01); *G01R 33/4812* (2013.01); *H01Q 1/22* (2013.01); *H01Q 7/00* (2013.01); *A61N 2005/1055* (2013.01)

(56) References Cited

U.S. PATENT DOCUMENTS

| | | |
|---|---|---|
| 2011/0169491 A1 | 7/2011 | Biber |
| 2012/0150016 A1 | 6/2012 | Rathee et al. |
| 2012/0286786 A1 | 11/2012 | Schellekens et al. |
| 2013/0027040 A1 | 1/2013 | Alagappan et al. |
| 2015/0077118 A1 | 3/2015 | Shvartsman et al. |
| 2015/0224341 A1 | 8/2015 | Vahala et al. |

\* cited by examiner

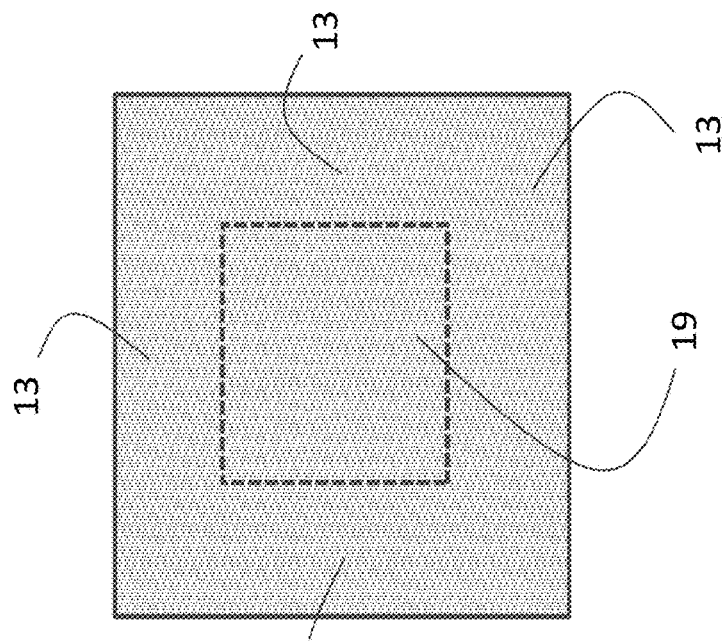
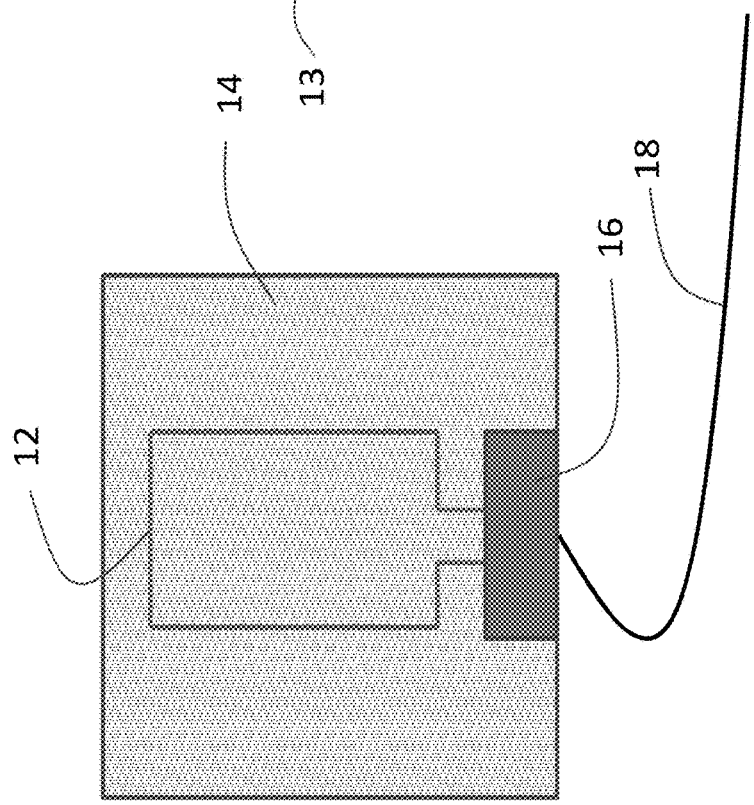

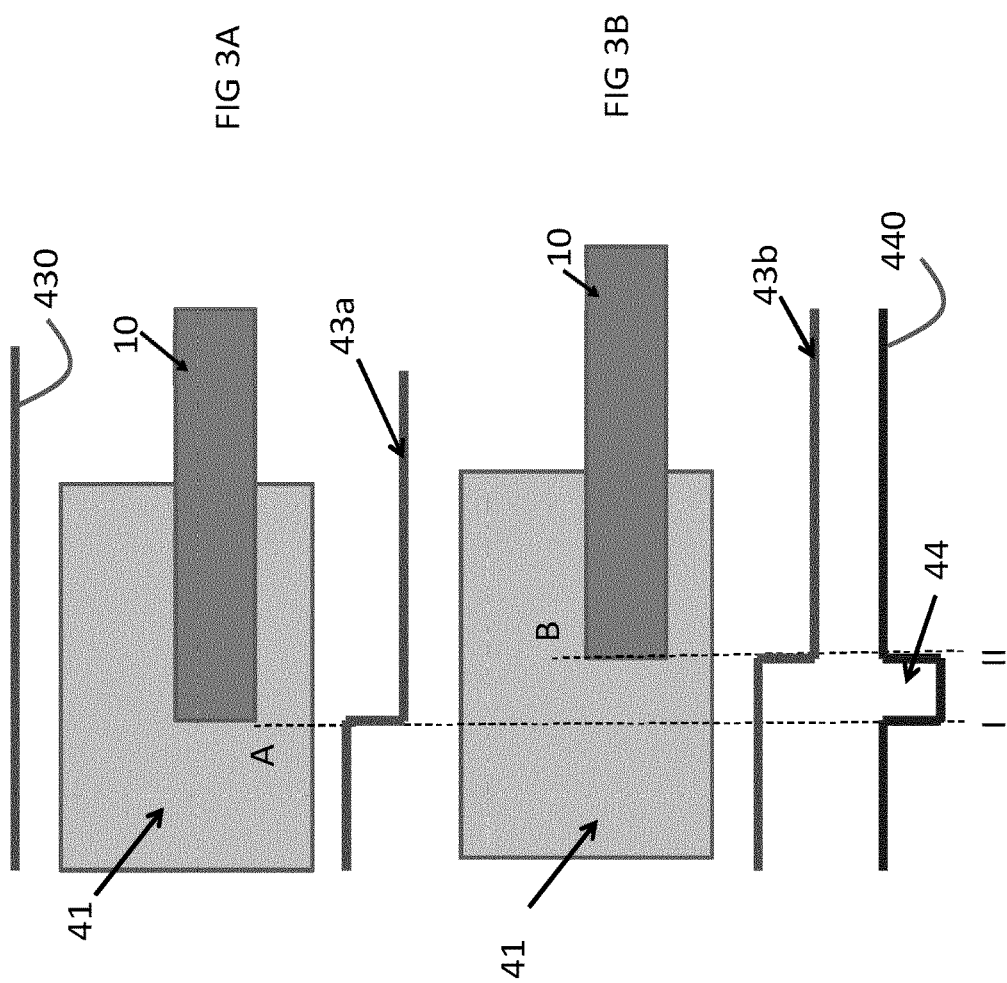

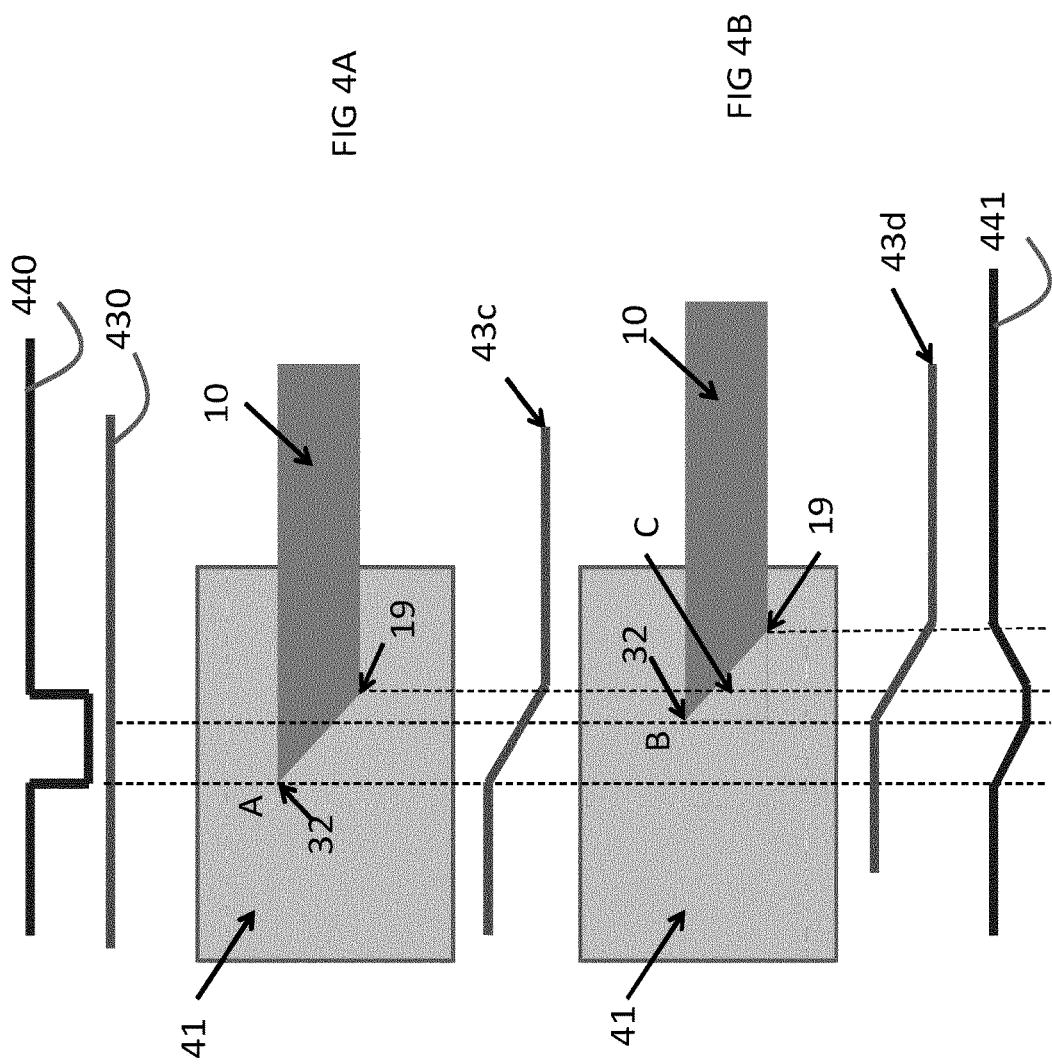

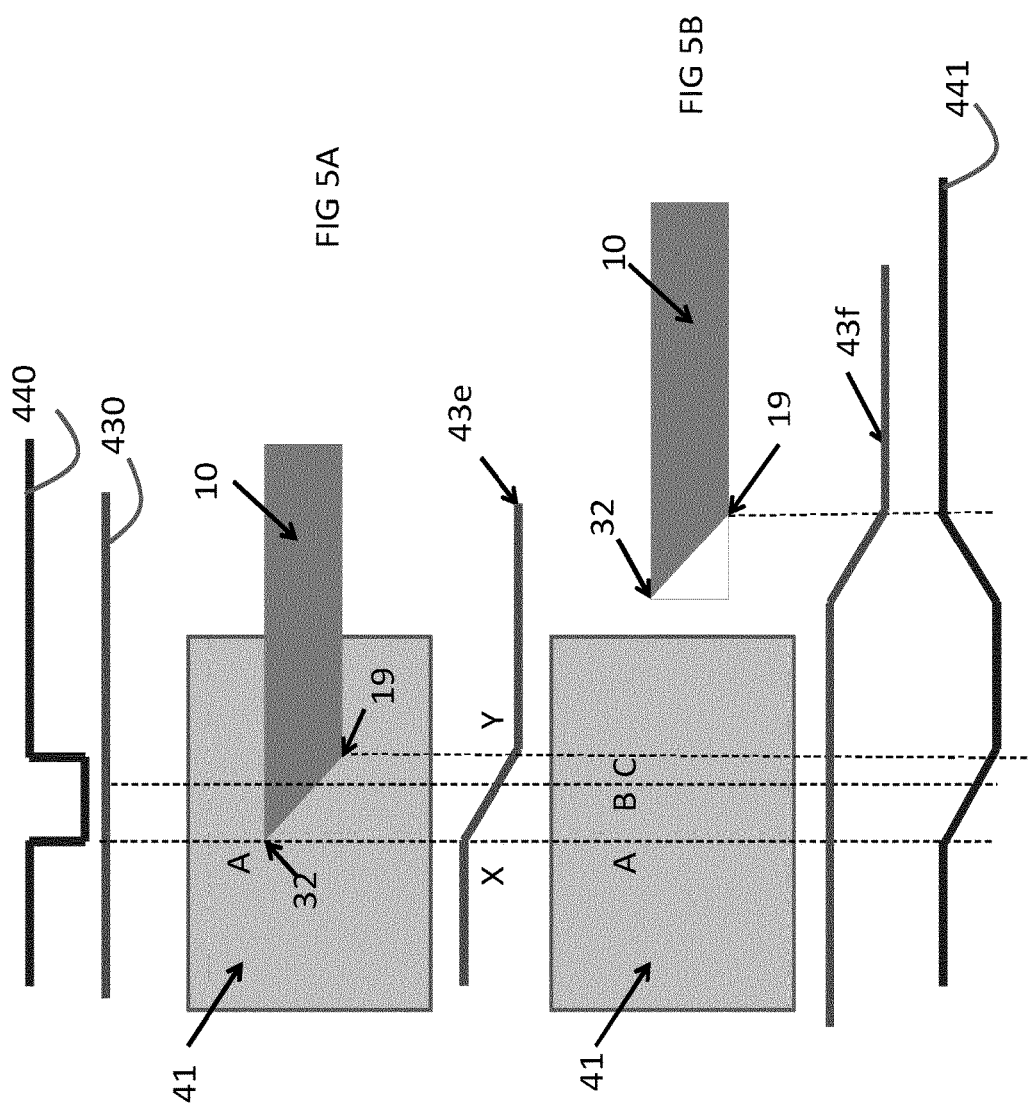

MAGNETIC RESONANCE TRANSMIT AND/OR RECEIVE ANTENNA SYSTEM AND RADIOTHERAPY PLANNING COMPUTER PROGRAM PRODUCT

CROSS REFERENCE TO RELATED APPLICATIONS

This application is a U.S. national phase application of International Application No. PCT/EP2015/069916, filed on Sep. 1, 2015, which claims the benefit of U.S. provisional Application Ser. No. 62/045,138 filed on Sep. 3, 2014 and EP Application Serial No. 14183412.7 filed Sep. 3, 2014, which are both incorporated herein by reference.

FIELD OF THE INVENTION

The invention relates to a device and computer program product in the field of magnetic resonance imaging. More particularly the inventions finds its application in magnetic resonance imaging guided radiotherapy.

BACKGROUND OF THE INVENTION

Conventional radiotherapy is based on CT and cone beam CT imaging for tumor and organ at risk delineation and for treatment guidance. Because of the superior soft tissue contrast of magnetic resonance imaging (MRI), MRI based radiotherapy is becoming increasingly popular. In order to achieve the best possible balance between tumor control and normal tissue complications, a radiation dose should be high in the tumor and as low as possible in the normal tissues. Furthermore, radiation dose delivery needs to be accurate and predictable, while at the same time maintaining sufficient MR image quality.

SUMMARY OF THE INVENTION

In general, embodiments of the disclosure are directed to address at least one of the above mentioned issues related to radiotherapy, while still achieving sufficient MR image quality.

One aspect of the disclosure is directed to a magnetic resonance transmit and/or receive antenna system configured for being used in combination with a magnetic resonance radiotherapy system. The antenna system comprises at least one antenna for transmitting and/or receiving radiofrequency signals, wherein the antenna comprises antenna components. The antenna system further comprises a cover enclosing the antenna components, wherein the enclosing cover has a spatially varying thickness and/or density towards an outer edge of the surface and/or next to an antenna component as to compensate for differences in radiation attenuation between the enclosing cover compared to the antenna component and/or air.

Another aspect of the disclosure is directed to a radiotherapy treatment planning computer program product configured for planning a magnetic resonance guided radiotherapy. The computer program product includes a planning module configured for calculating settings for a radiotherapy system such that when these settings are used during radiotherapy a delivered dose distribution resembles a planned fluence distribution within a predetermined range. Further, the computer program product includes an antenna system information module comprising information regarding the position and/or spatial variations in thickness and/or density of the antenna system. The planning module is configured for taking a position or spatial variations in thickness and/or spatial variation in density of a transmit or receive antenna system into account and calculating the settings to compensate for differences in radiation attenuation between an enclosing cover and radiation coefficients of air or an antenna component. The computer program product may be configured to be used in combination with any of the herein disclosed antenna systems.

During MRI guided radiotherapy transmit and/or receive antenna systems may be placed on or close to a patient to be treated. This positioning of the antenna close to the patient improves the image quality. However, by doing so in an MR guided radiotherapy setting, the antenna system itself is placed directly in the radiation beam path and is exposed to high radiation fluence. Part of the radiation beam may travel through the antenna system, whereas another part of the radiation beam may not travel through the antenna system. Due to differences in radiation attenuation coefficient between air and the antenna system, the antenna system will attenuate the beam more than the surrounding air. Therefore, a presence of the antenna system in the radiation beam may cause sudden changes in a dose profile measured behind the antenna system inside the patient.

The antenna system comprises at least one antenna. The antenna comprises antenna components such as conductors. The antenna preferably is a coil. The antenna system further comprises a cover enclosing antenna components. Also the radiation attenuation coefficients, and thereby the resulting radiation attenuation, between the enclosing cover and the antenna and its components may differ. Therefore, also the presence of antenna components may cause sudden changes in a dose profile measured behind the antenna system inside the patient. These effects may decrease the accuracy of the dose delivered during radiotherapy, and may make the actual dose delivered more dependent on an exact positioning of the antenna system. These effects can be compensated for by varying the thickness and/or density of the enclosing cover towards an outer edge of a surface formed by the enclosing cover and varying the thickness and/or density of the enclosing cover next to an antenna component.

According to an embodiment of the disclosure, the thickness and/or density of the enclosing cover decreases in a direction from a center part of the enclosing cover towards an outer edge. The change in attenuation, when the beam crosses the border between air and an edge of the antenna system, can cause a sudden change in fluence profile, resulting in an undesired dose delivery. A decreasing thickness and/or density of the enclosing cover in a direction from the center part towards the edge reduces the undesirable sudden change in fluence profile. In an embodiment, the decrease in thickness and/or density of the enclosing cover is preferably gradual. This makes a delivered dose distribution less sensitive to errors in the placement of the antenna system, which in turn makes radiation dose delivery more accurate and predictable.

According to an embodiment of the disclosure, the thickness and/or density of the enclosing cover increases substantially near and in a direction towards an antenna component. For example, antenna components likely have a higher radiation attenuation coefficient than the surrounding enclosing cover. Therefore, the presence of antenna components such as conductors may cause sudden density peaks in the antenna system, which in turn may result in a steep increase in radiation attenuation. By increasing the thickness and/or density of the enclosing cover substantially near and in a direction towards the antenna component, the sudden density peak caused by the antenna component can be compensated for. Therefore, the sudden and strong increase in radiation attenuation caused by the antenna system can be made more gradual.

If for example a radiation beam passing through the antenna system is adjusted to compensate for attenuation of the coil by the radiotherapy treatment planning computer program, the transition between air and the enclosing cover causes less of an undesired behavior in delivered dose. Combining this adjustment of the radiation beam to compensate for attenuation of the antenna system with an antenna system having a decreasing thickness and/or density of the enclosing cover in a direction from the center part towards the edge may further reduce such undesired behaviors. In a similar way, the effects of radiation attenuation caused by the presence of one or more antenna components can be compensated for.

Additional objects and advantages of the present disclosure will be set forth in part in the following detailed description, and in part will be obvious from the description, or may be learned by practice of the present disclosure. The objects and advantages of the present disclosure will be realized and attained by means of the elements and combinations particularly pointed out in the appended claims.

It is to be understood that the foregoing general description and the following detailed description are exemplary and explanatory only, and are not restrictive of the invention, as claimed. These and other aspects of the invention will be apparent from and elucidated with reference to the embodiments described hereinafter.

BRIEF DESCRIPTION OF THE DRAWINGS

The accompanying drawings, which constitute a part of this specification, illustrate several embodiments and, together with the description, serve to explain the disclosed principles.

FIGS. 1A and 1B diagrammatically show an antenna system for use in magnetic resonance imaging.

FIGS. 3A and 3B diagrammatically show the effects of positioning of the antenna system into the radiation beam.

FIGS. 4A and 4B diagrammatically show the effects of an antenna system with increasing thickness and density on radiation attenuation for different situations.

FIGS. 5A and 5B diagrammatically show the effects of changing the position of an antenna system having an increasing thickness and density on radiation attenuation.

DETAILED DESCRIPTION OF EMBODIMENTS

Figure 2:
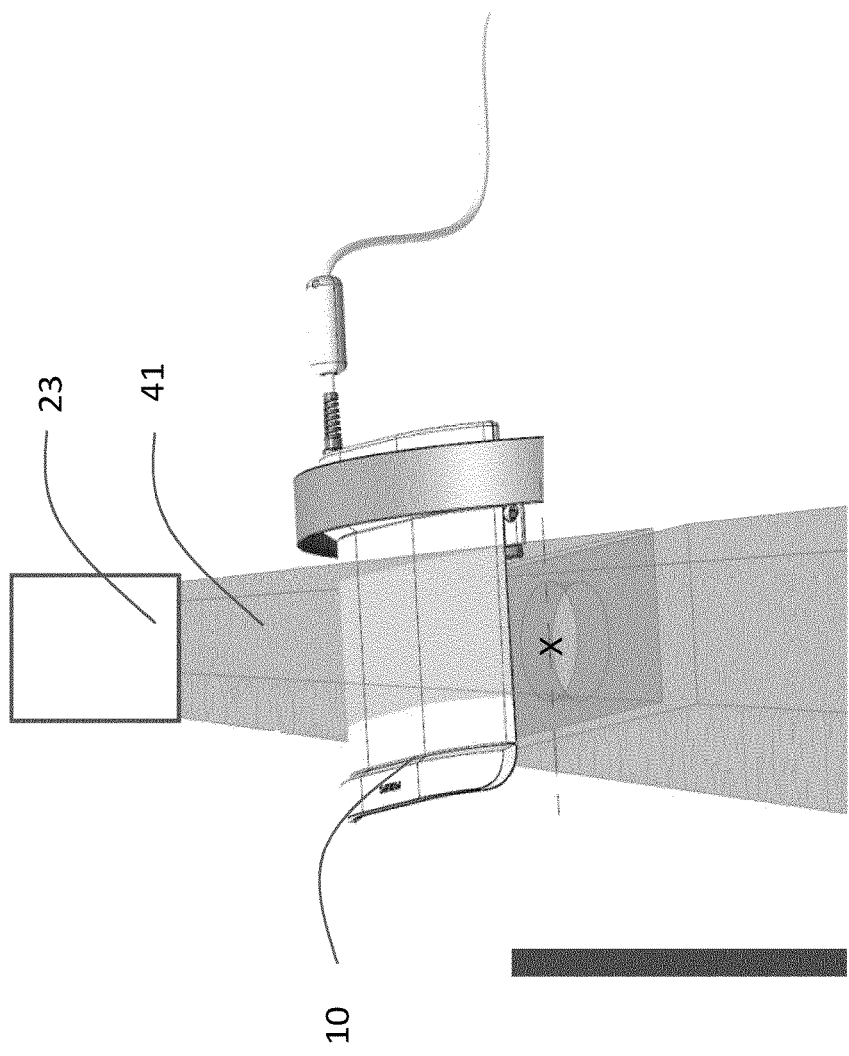
FIG. 2 diagrammatically exemplary shows a transmit and/or a receive antenna system being used during radiotherapy.

Exemplary embodiments are described with reference to the accompanying drawings. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. And the singular forms "a," "an," and "the" include plural references unless the context clearly dictates otherwise.

FIG. 1A diagrammatically shows antenna system 10 for use in magnetic resonance imaging. The antenna system 10 comprises an antenna 12 and an enclosing cover 14 for protecting and/or supporting the antenna 12. The antenna system 10 further comprises electronics 16 and a cable 18, e.g., for powering the antenna system. The enclosing cover 14 as shown in FIG. 1B, comprises a center part 19 and four outer edges 13.

Figure 8:
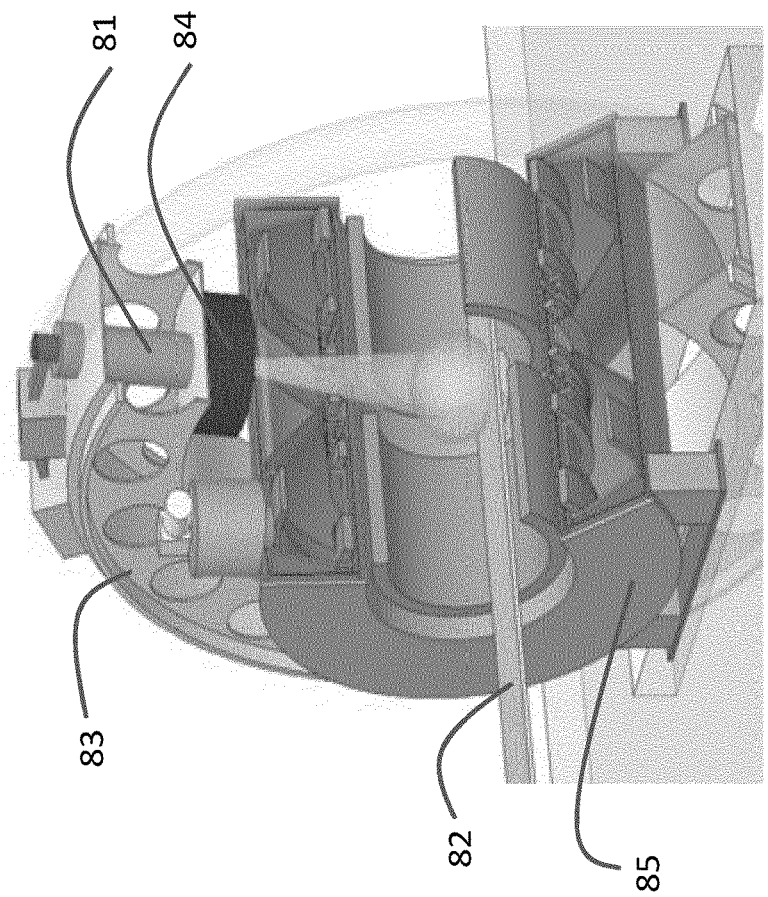
FIG. 8 diagrammatically shows an embodiment of a MRI-linear accelerator used with the radiotherapy treatment planning computer program product of FIG. 7.

FIG. 2 diagrammatically shows how a transmit and/or a receive antenna system 10 could be used during radiotherapy. The antenna system 10 is positioned within the bore of an MRI radiotherapy system on an upper or under side of a patient (not shown). An exemplary MRI radiotherapy system is shown in FIG. 8. The radiotherapy system 23 is in this case a linear accelerator, but could for example, also be any other x-ray or gamma ray emitting system. The linear accelerator generates a beam of x-rays 41, which travels through the antenna system 10 to the patient positioned below the antenna system 10 at position X. The receive coils of the MRI system are placed close to the treated and imaged anatomy to maximize image quality and enable the MRI radiotherapy system to provide efficient MR guidance for the radiation beam. As a consequence the receive coils are located in the radiation beam path, which results in the coils attenuating the beam and also cause non-idealities in the radiation therapy that have to be taken into account during the delivery of the radiation treatment.

FIG. 3 diagrammatically shows the effects of positioning of the antenna system 10 into the radiation beam. The antenna system 10 is positioned in an x-ray beam 41 as shown in FIG. 2. Returning to FIG. 3, for example, a constant desired fluence may be desired by the radiation therapy treatment planning system (See FIG. 7). When creating a treatment plan, an assumption is made that the antenna system 10 may be located at a known location during treatment delivery. In practice, when the antenna is placed into the radiotherapy system 23 at treatment delivery time, it may be located several millimeters away from the known location assumed by the treatment plan. Because of this change in location, the treatment planning system is unable to correct for the antenna's "true" location at treatment delivery time in order to provide the correct level of radiation fluence.

As shown in FIG. 3A, the presence of the antenna system 10, affects the desired fluence 430. One end of the antenna system 10 is positioned at a first position "A" corresponding to line position I. A corresponding fluence profile (e.g., as known in the art, fluence is an energy density per unit area per unit time) between the antenna system 10 and the patient, when the antenna system 10 is positioned at "A" is illustrated by line 43a. The presence of the antenna system 10 causes a dip in the fluence profile at location I, as shown by line 43a. The sudden change in the fluence profile at location I (e.g., a step in attenuation profile) is unfavorable. FIG. 3B illustrates the movement of the antenna system 10 from the first position "A" (assumed by the treatment planning system) to a second position "B" (e.g., actual position at treatment time). The change in position of the antenna system 10 results in a change in the fluence profile at location II, as shown by line 43b. The presence of the antenna system 10 causes an undesired attenuation of the radiation beam 41, which needs to be mitigated. The fluence profile is highly dependent on the exact position of the antenna system 10 (e.g., receive coils) that is located in the radiation beam path 41. As illustrated by the error curve 440, there is a sudden dip 44, corresponding to the attenuation of the antenna system 10, in the fluence that is provided. The attenuation causes non-idealities in the radiation fluence when the "true" location of the coil (e.g., the coil's location at treatment delivery time), is not known to the radiation therapy planning system.

FIG. 4 diagrammatically shows the effects of an antenna system 10 with increasing thickness and density on radiation attenuation for different positions of the antenna system 10 in the radiation beam 41. Similar to FIG. 3, FIG. 4 exemplary illustrates one embodiment where the fluence desired by the radiation planning system is constant 430. The error curve 440 from FIG. 3 is repeatedly illustrated in FIG. 4 for convenience. What is desired is for the antenna system to decrease the magnitude of the error on the radiation beam 41.

FIG. 4A shows the antenna system 10 according to an embodiment of the disclosure, where the thickness of the enclosing cover gradually and monotonously decreases in a direction from a center part 19 towards an outer edge 32. In an embodiment, the enclosing cover has a tapered edge (e.g., the tapering may be on the inside (bottom), outside (top), or both). In a preferred embodiment the taper may be on the top (e.g., outside). As a result, there is still attenuation caused by the antenna system 10 at the location of the coil (see fluence profile 43c). But, because of the varying thickness of the enclosing cover, the degree of attenuation occurs more gradually. Minimizing the undesired behavior due to the antenna system's actual location at treatment delivery time 10 in the beam path 41 is achieved by making the depth of the Desired Error curve 441 shallower than the depth of the Undesired Error curve 440. This is achieved by utilizing an antenna system 10 having a change in thickness (or density).

As discussed above, the antenna system 10 typically has some movement from the assumed first position "A" (e.g., the position assumed by the treatment planning system) to a second position "B" (e.g., the actual position at treatment delivery time), shown in FIG. 4B. Therefore, the fluence profile changes, as shown by lines 43c and 43d. The advantage, as shown by the desired error curve 441, is that any attenuation caused by the antenna system is spread out and exhibits a shallower depth.

FIG. 5 diagrammatically shows in an embodiment an effect to the fluence when the position of the tapered section of the antenna system 10 assumed by the treatment planning system does not overlap with the tapered section of the antenna system when the antenna system is placed at treatment delivery time. As previously illustrated in FIGS. 3 and 4 and shown for convenience in FIG. 5, the desired fluence 430 is constant and the undesired error 440 is a dip in the fluence. Further, FIG. 5A illustrates the antenna system 10 positioned at a position "A" assumed by the treatment planning system, where the antenna system 10 has thickness of the enclosing cover gradually decreasing in a direction from a center part 19 towards an outer edge 32. The resulting fluence is illustrated by curve 43e. As shown by curve 43e, the fluence drops from point X to a point Y. This drop in fluence has a depth corresponding to the attenuation of the antenna system 10.

FIG. 5B diagrammatically shows an embodiment where the antenna system 10 can be moved far enough to make the position of the tapered section of the antenna system assumed by the treatment planning system not overlap with the tapered section of the antenna system when the antenna system is placed at treatment delivery time. Curve 43f illustrates a corresponding fluence. In order to make the Desired Error curve 441 shallower, the length of the tapered section of the antenna system must be greater than or equal to the expected error between the assumed and the actual antenna system locations.

The effect of any imprecision with regard to the mechanical placement of the antenna system 10 (e.g., 3-5 cm) may be minimized by utilizing the antenna system with a change in thickness or density (e.g., or tapering). In an embodiment, the longer the taper section, the shallower the depth of the error curve 441.

Figure 6A:
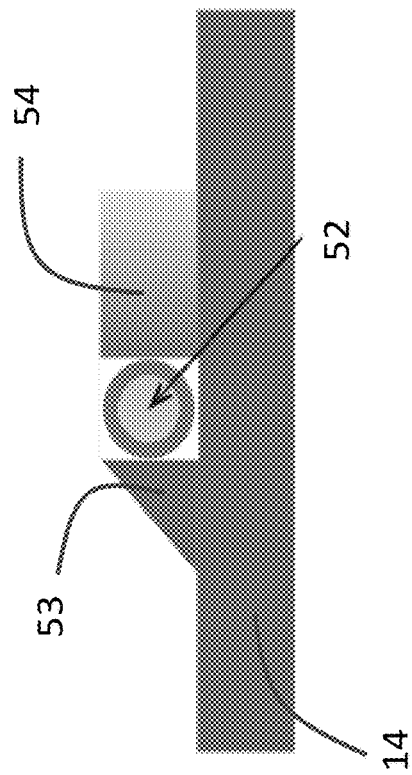
FIGS. 6A and 6B diagrammatically show a transmit and/or receive antenna system with increasing thickness and density of the enclosing cover near and towards an antenna component.
Figure 6B:
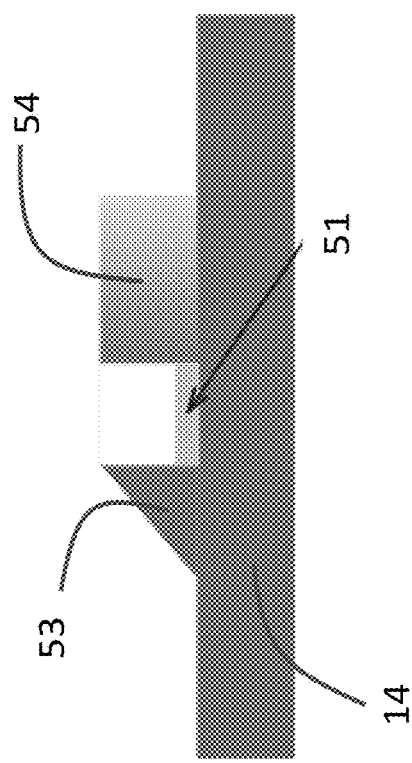

FIG. 6 diagrammatically shows a transmit and/or receive antenna system with increasing thickness and density near and towards an antenna component. FIG. 6A shows an antenna system comprising high density conductor material in the form of a PCB trace 51, and FIG. 6B shows an antenna system comprising high density conductor material in the form of a wire 52. Because both antenna components (e.g., the PCB trace 51 and the high density wire 52) have a higher radiation attenuation coefficient compared to the enclosing cover 14, a difference between the delivered fluence and the desired fluence planned by the treatment planning system occurs due to the fact that the antenna components locations at treatment delivery time are different from where the treatment planning system assumed they are. Minimizing the effect can be performed by either an increase in the thickness 53 of the enclosing cover substantially near and in a direction towards the antenna component or an increase in density 54 of the enclosing cover substantially near and in a direction towards the antenna component.

Figure 7:
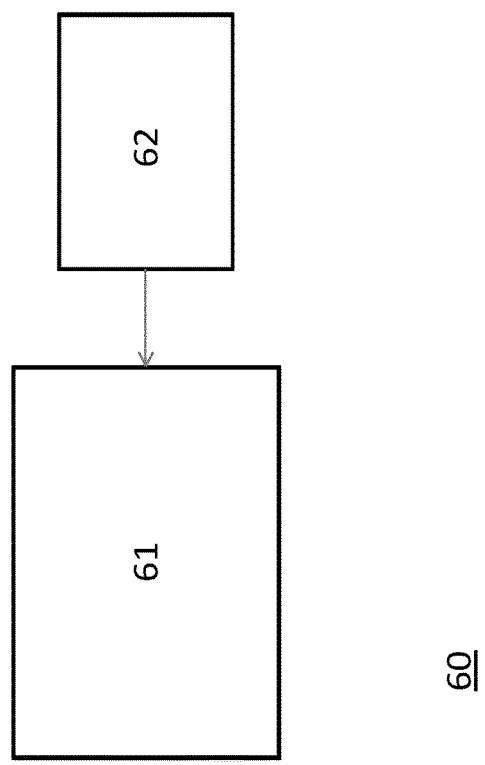
FIG. 7 diagrammatically shows a radiotherapy treatment planning computer program product configured for planning a magnetic resonance guided radiotherapy.

FIG. 7 diagrammatically shows a radiotherapy planning computer program product configured for planning a magnetic resonance guided radiotherapy. The radiotherapy planning computer program product 60 comprises a planning module 61 configured for calculating settings for a radiotherapy system, such that, when these settings are used during radiotherapy a delivered fluence distribution resembles a planned fluence distribution within a predetermined range. The planning module 61 receives information from an antenna system information module 62 regarding the position and/or spatial variations in thickness and/or density of the antenna system. The planning module 61 is configured for taking into account a position and/or spatial variations in thickness and/or density of the antenna system and calculating the settings such as to compensate for differences in radiation attenuation between the enclosing cover and air and/or an antenna component (e.g., at the boundary between air and the edge of the coil, there is a sudden step in attenuation causing inconsistent fluence delivery). For example the calculated settings could be such that a fluence gradient will be placed near the outer edge of the antenna system during treatment.

FIG. 8 illustrates an embodiment of a radiotherapy device 23, an MRI-linear accelerator (MRI 85) that works with a radiotherapy planning computer program product of FIG. 7. In an embodiment by using a linear accelerator 81, a patient may be positioned on a patient table 82 to receive the radiation fluence determined by the treatment plan. Linear accelerator may include a radiation head 84 that generates a radiation beam. The entire radiation head may be rotatable around a horizontal axis. The intersection of the axis with the center of the beam, produced by the radiation head, is usually referred to as the "isocenter". The patient table 82 may be motorized so that the patient can be positioned with the tumor site at or close to the isocenter. The radiation head 84 may be mounted on a rotating gantry 83, to provide patient with a plurality of varying dosages of radiation according to the treatment plan.

While the invention has been illustrated and described in detail in the drawings and foregoing description, such illustrations and description are to be considered illustrative or exemplary and not restrictive. Moreover, it will be apparent to those skilled in the art to consider the specification and the practice of the present disclosure that various modifications and variations can be made to the disclosed systems, products and methods without departing from the scope of the disclosure, as claimed. Thus, it is intended that the specification and examples be considered as exemplary only, with a true scope of the present disclosure being indicated by that following claims and their equivalents.

The invention claimed is:

1. A magnetic resonance imaging (MRI) antenna system configured for use with a magnetic resonance guided radiotherapy system that emits radiation at treatment delivery time during MRI imaging, the antenna system comprising:
    at least one antenna for transmitting and/or receiving radiofrequency signals during the MRI imaging, wherein the antenna comprises antenna components; and
    a cover enclosing the antenna components, the cover comprising a center part and an outer edge, wherein a thickness and/or density of the cover decreases in a direction from the center part towards the outer edge to compensate for differences in radiation attenuation of the radiation emitted by the radiotherapy system between the cover and air.

2. The MRI antenna system as claimed in claim 1, wherein the cover comprises a tapered edge tapered in the direction from the center part towards the outer edge.

3. The MRI antenna system as claimed in claim 1, wherein the thickness and/or density of the cover increases near and in a direction towards the antenna components enclosed by the cover.

4. A radiotherapy planning non-transitory computer program product configured for planning magnetic resonance guided radiotherapy using a radiotherapy device for emitting a radiation beam, together with a magnetic resonance imaging (MRI) system having an MRI antenna system, the MRI antenna system comprising an antenna for transmitting and/or receiving radiofrequency signals during MRI imaging by the MRI system, and a cover enclosing components of the antenna and comprising a center part and an outer edge, a thickness and/or density of the cover decreasing in a direction from the center part towards the outer edge to compensate for differences in radiation attenuation of the radiation emitted by the radiotherapy device, the computer program product comprising:
    a planning module configured for calculating settings for the radiotherapy device such that use of the calculated settings during the guided radiotherapy delivers a fluence distribution that resembles a planned fluence distribution within a predetermined range; and
    an antenna system information module comprising information regarding variations in the thickness and/or variations in the density of the cover of the antenna system, the thickness and/or the density of the cover decreasing in the direction from the center part towards the outer edge,
    wherein the planning module is further configured for taking the position and/or spatial variations in thickness and/or density of the antenna system into account and calculating settings to compensate for differences in the radiation attenuation between the cover and radiation coefficients of air.

5. The radiotherapy planning computer program product as claimed in claim 4, wherein the variations in the thickness and/or the density of the cover of the antenna system cause spatial variations of the attenuation of the radiation beam to be gradual.

6. An antenna system in a magnetic resonance imaging (MRI) system for MRI imaging, configured for use with a magnetic resonance guided radiotherapy system, which emits a radiation beam for radiation therapy treatment during the MRI imaging, the antenna system comprising:
    an antenna for transmitting and/or receiving radiofrequency signals during the MRI imaging and the radiation therapy treatment; and
    a cover enclosing at least portions of the antenna and comprising a center part and an outer edge, wherein a thickness and/or density of the cover decreases in a direction from the center part towards the outer edge, reducing radiation attenuation of the radiation beam emitted by the radiotherapy system towards the outer edge.

7. The antenna system as claimed in claim 6, wherein the thickness and/or density of the cover increases towards the portions of the antenna enclosed by the cover.

* * * * *